(12) United States Patent
Weber et al.

(10) Patent No.: US 6,518,471 B1
(45) Date of Patent: Feb. 11, 2003

(54) SELECTIVE PRODUCTION OF META-DIISOPROPYLBENZENE

(75) Inventors: William A. Weber, Marlton, NJ (US); Charles Morris Smith, Houston, TX (US); Francis S. Bryan, Townsend, DE (US); Stephen H. Brown, Brussels (BE); Jane C. Cheng, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/891,323

(22) Filed: Jun. 25, 2001

(51) Int. Cl.[7] .................................................. C07C 5/22
(52) U.S. Cl. ........................................ 585/475; 585/481
(58) Field of Search ................................... 585/475, 481

(56) References Cited

U.S. PATENT DOCUMENTS

| | | | | |
|---|---|---|---|---|
| 2,768,985 A | | 10/1956 | Schlatter | 260/671 |
| 2,848,514 A | | 8/1958 | Keiser et al. | 260/671 |
| 3,308,069 A | * | 3/1967 | Wadlinger et al. | 252/455 |
| 3,766,093 A | * | 10/1973 | Chu | 252/455 Z |
| 3,780,123 A | * | 12/1973 | Suggitt | 260/672 T |
| 3,894,104 A | * | 7/1975 | Chang et al. | 260/668 R |
| 4,439,409 A | * | 3/1984 | Puppe et al. | 423/328 |
| 4,822,943 A | * | 4/1989 | Burress | 585/467 |
| 4,826,667 A | * | 5/1989 | Zones et al. | 423/277 |
| 4,954,325 A | * | 9/1990 | Rubin et al. | 423/328 |
| 4,962,257 A | * | 10/1990 | Absil et al. | 585/475 |
| 4,992,606 A | * | 2/1991 | Kushnerick et al. | 585/467 |
| 5,198,595 A | * | 3/1993 | Lee et al. | 585/467 |
| 5,236,575 A | * | 8/1993 | Bennett et al. | 208/46 |
| 5,243,116 A | * | 9/1993 | Lee et al. | 585/467 |
| 5,250,277 A | * | 10/1993 | Kresge et al. | 423/329 |
| 5,329,059 A | * | 7/1994 | Marler | 585/475 |
| 5,362,697 A | * | 11/1994 | Fung et al. | 502/71 |
| 5,488,194 A | | 1/1996 | Beck et al. | 585/475 |
| 6,049,018 A | * | 4/2000 | Calabro et al. | 585/446 |

FOREIGN PATENT DOCUMENTS

| | | |
|---|---|---|
| WO | 01/21562 | 3/2001 |
| WO | 02/26671 | 4/2002 |

* cited by examiner

*Primary Examiner*—Thuan D. Dang
(74) *Attorney, Agent, or Firm*—Darryl M. Tyus

(57) ABSTRACT

In a process for the selective production of meta-diisopropylbenzene, a $C_9$+aromatic hydrocarbon feedstock containing meta- and ortho-diisopropylbenzene is contacted with benzene under conversion conditions with a catalyst comprising a molecular sieve selected from the group consisting of zeolite beta, mordenite and a porous crystalline inorganic oxide material having an X-ray diffraction pattern including the d-spacing maxima at 12.4±0.25, 6.90±15, 3.57±0.07 and 3.42±0.07 Angstrom. The contacting step selectively converts ortho-diisopropylbenzene in the feedstock to produce an effluent in which the ratio of meta-diisopropylbenzene to ortho-diispropylbenzene is greater than that of the feedstock. The effluent is the fed to a separation zone for recovery of a product rich in meta-diisopropylbenzene.

7 Claims, No Drawings

SELECTIVE PRODUCTION OF META-DIISOPROPYLBENZENE

This invention is directed to a process for the selective production of meta-diisopropylbenzene (DIPB).

BACKGROUND OF THE INVENTION

Meta-DIPB is an important intermediate in organic synthesis. Thus resorcinol can be prepared by oxidizing meta-DIPB with air and then decomposing the resulting dihydroperoxide with acid. However, although para-DIPB can be separated from a mixture of PIDB isomers by super fractionation, the boiling points of ortho- and meta-DIPB are too close to allow effective separation of meta-DIPB by fractionation. Moreover, ortho-DIPB is not readily oxidized and hence builds up in the production loop, requiring removal as a purge and representing a yield loss. Thus, to be commercially viable, any process for producing meta-DIPB must minimize the production of the ortho-isomer.

Currently, meta-DIPB is manufactured commercially by alkylating cumene with propylene over a homogeneous $AlCl_3$ catalyst. The high activity of the $AlCl_3$ catalyst produces a mixture of DIPB isomers with near equilibrium ortho content. This is advantageous since at equilibrium in the liquid phase between 50 and 150° C. the ratio of meta:ortho DIPB is greater than 100 providing sufficient purity for efficient downstream conversion to resorcinol. Process operation between 50 and 150° C. also results in DIPB products containing less than 1000 ppm of co-boiling n-propyl-isopropylbenzene and trimethylindane impurities. However, corrosion and the need to neutralize, separate and recycle the $AlCl_3$ catalyst, make this process difficult to practice.

DIPB can also be produced by separation from the polyalkylated by-product of the alkylation of benzene with propylene to produce cumene over a heterogeneous catalyst, such as a molecular sieve. However, DIPB separated from the polyalkylated fraction of current commercial cumene plants is rich in the kinetically preferred para- and ortho-DIPB isomers, making this route of limited use in the synthesis of meta-DIPB, unless the ortho- and para-content is reduced by, for example, isomerization or transalkylation. Transalkylation and isomerization, however, can introduce contaminant n-propyl-isopropylbenzenes and trimethylindanes.

Accordingly, there is an outstanding need for a heterogeneous process for producing high purity DIPB's near their equilibrium distribution (rich in the meta-isomer and substantially free of the ortho-isomer and impurities such as n-propylisopropylbenzenes and trimethylindanes.)

U.S. Pat. No. 4,992,606 discloses a process for preparing short chain ($C_1$–$C_5$) alkylaromatic compounds by alkylation of an aromatic compound, such as benzene and cumene, with a short chain alkylating agent, such as propylene, over the molecular sieve MCM-22. In addition, U.S. Pat. No. 4,962,257 discloses the use of MCM-22 in the disproportionation of toluene to xylenes.

U.S. Pat. No. 5,329,059 discloses a process for the disproportionation of an alkylaromatic compound, wherein the alkyl group has from 1 to about 6 carbon atoms, e.g., cumene, by contacting said compound with catalyst comprising an active form of synthetic porous crystalline MCM-49. MCM-49 is one of a family of molecular sieves which, together with MCM-36 and MCM-56, have certain structural similarities with MCM-22.

U.S. Pat. No. 4,822,943 discloses a process for the selective production of para-DIPB by reacting cumene and/or benzene with propylene over the molecular sieve ZSM-12.

U.S. Pat. No. 5,198,595 discloses a process for preparing alkylaromatic compounds by alkylation of an aromatic compound with an alkylating agent having two to eighteen carbon atoms, such as propylene, over mordenite which has been subjected to repeated calcination and acid treatment so as to have a silica/alumina molar ratio of at least 40:1.

U.S. Pat. No. 6,049,018 discloses the porous crystalline material MCM-68 and its use in the alkylation of aromatics with short chain ($C_2$–$C_6$) olefins (for example, the alkylation of benzene with ethylene or propylene to produce ethylbenzene or cumene respectively), the transalkylation of aromatics (for example, the transalkylation of polyethylbenzenes or polyisopropytbenzenes with benzene to produce ethylbenzene or cumene respectively), and the disproportionation of alkylaromatics (for example, the disproportionation of toluene to produce xylenes).

U.S. Pat. No. 3,780,123 discloses the catalytic disproportionation of alkylbenzenes, including cumene, by contacting the alkylbenzene and a sulfide compound with hydrogen mordenite containing a sulfided Group VIII metal. According to Table 1 of U.S. Pat. No. 3,780,123, when mordenite is used to disproportionate cumene in the presence of methyldisulfide as the sulfide compound, the process produces a mixture of DIPB isomers in which the meta:ortho isomer ratio is between 58 and 85 and the product contains 4.4–7.2 wt % n-propylbenzene and 4.4–5.2 wt % of unidentified impurities. As a co-boiler with cumene, n-propylbenzene is an undesirable impurity, particularly since, on disproportionation, it yields n-propylisopropylbenzenes which tend to co-boil with meta-DIPB.

It will, of course, be understood that the disproportionation of cumene to produce DIPB and benzene is the inverse of the transalkylation of DIPB with benzene to produce cumene.

According to the invention, it has now been found that if a mixture of DIPB isomers, such as that produced by a commercial cumene plant, is contacted under conversion conditions with benzene, either alone or in combination with cumene, in the presence of a molecular sieve selected from an MCM-22 family molecular sieve, zeolite beta and mordenite, the ortho-DIPB and/or the para-DIPB in the mixture are selectively converted. Depending on the composition of the feedstock the conversion occurs by transalkylation or a combination of transalkylation and isomerization. As a result, the process of the invention provides a heterogeneous route to the production of a meta-rich DIPB product in which the meta:ortho ratio is in excess of 100, and preferably in excess of 200. Moreover, the production of impurities which coboil with meta DIPB is very low, typically less than 0.5 wt % of the DIPB product.

SUMMARY OF THE INVENTION

In one aspect, the invention resides in a process for the selective production of meta-diisopropylbenzene, said process comprising the steps of:

(a) contacting a $C_9$+ aromatic hydrocarbon feedstock containing meta-and ortho-diisopropylbenzene with benzene under conversion conditions with a catalyst comprising a molecular sieve selected from the group consisting of zeolite beta, mordenite and a porous crystalline inorganic oxide material having an X-ray diffraction pattern including the d-spacing maxima at 12.4±0.25, 6.9±0.15, 3.57±0.07 and 3.42±0.07 Angstrom, said contacting step selectively converting ortho-diisopropylbenzene in the feedstock to produce an effluent in which the ratio of meta-diisopropylbenzene to ortho-diisopropylbenzene is greater than that of the feedstock; and then (b) feeding said effluent to a separation zone to recover from said effluent a product rich in meta-diisopropylbenzene.

Preferably, said porous crystalline inorganic oxide material is selected from the group consisting of MCM-22, PSH-3, SSZ-25, MCM-36, MCM-49 and MCM-56.

Preferably, said porous crystalline inorganic oxide material is MCM-22.

Preferably, said feedstock is contacted in step (a) with benzene and cumene.

Preferably, said conversion conditions include a temperature of about 100 to about 250° C., a pressure of about 50 to about 1000 psig, and a WHSV of about 0.1 to about 100.

More preferably, said conversion conditions include a temperature of about 120 to about 200° C., a pressure of about 200 to about 500 psig, and a WHSV of about 0.5 to about 5.

In a further aspect, the invention resides in a process for the selective production of meta-diisopropylbenzene, said process comprising the steps of:

(a) alkylating benzene with propylene under alkylation conditions in the presence of a solid alkylation catalyst to produce an alkylation product comprising unreacted benzene, cumene and diisopropylbenzene isomers; then (b) contacting at least part of said alkylation product under conversion conditions with a further catalyst comprising a molecular sieve selected from the group consisting of zeolite beta, mordenite and a porous crystalline inorganic oxide material having an X-ray diffraction pattern including the d-spacing maxima at 12.4±0.25, 6.9±0.15, 3.57±0.07 and 3.42±0.07 Angstrom, said contacting step selectively converting ortho-diisopropylbenzene in the alkylation product to produce an effluent in which the ratio of meta-diisopropylbenzene to ortho-diisopropylbenzene is greater than that of the alkylation product; and then (c) feeding said effluent to a separation zone to recover from said effluent a product rich in meta-diisopropylbenzene.

Preferably, the molar ratio of benzene to propylene in said alkylating step is greater than 1 but less than 2.5.

Preferably, said solid alkylation catalyst comprises a molecular sieve selected from the group consisting of zeolite beta and a porous crystalline inorganic oxide material having an X-ray diffraction pattern including the d-spacing maxima at 12.4±0.25, 6.9±0.15, 3.57±0.07 and 3.42±0.07 Angstrom.

Preferably, said solid alkylation catalyst comprises a molecular sieve selected from the group consisting of MCM-22, PSH-3, SSZ-25, MCM-36, MCM-49 and MCM-56.

Preferably, said alkylation conditions include a temperature of about 50 to about 150° C., a pressure of about 100 to about 1000 psig, and a WHSV of about 0.1 to about 100.

More preferably, said alkylation conditions include a temperature of about 100 to about 140° C., a pressure of about 200 to about 500 psig, and a WHSV of about 0.5 to about 10.

DETAILED DESCRIPTION OF THE INVENTION

The present invention provides a process for the selective production of high purity meta-diisopropylbenzene (DIPB) by contacting a $C_9$+aromatic hydrocarbon feedstock containing meta-, ortho- and, in certain embodiments, para-DIPB with benzene, or benzene and cumene, under conversion conditions with a catalyst comprising a molecular sieve selected from the group consisting of zeolite beta, mordenite and a porous crystalline inorganic oxide material having an X-ray diffraction pattern including the d-spacing maxima at 12.40±0.25, 6.9±0.15, 3.57±0.07 and 3.42±0.07 Angstrom. The contacting step selectively converts ortho-DIPB and, if present, para-DIPB in the feedstock to produce an effluent in which the ratio of meta-DIPB to ortho-DIPB is greater than that of the feedstock (nearer to equilibrium). By feeding the effluent to a separation step, such as a super-fractionation unit, it is possible to recover a DIPB product in which the meta:ortho ratio is in excess of 100, and preferably in excess of 200 and the level of impurities which coboil with meta DIPB is less than 0.5 wt % of the DIPB product.

The catalyst employed in the process of the invention employs as the active material at least one molecular sieve selected from the group consisting of zeolite beta, mordenite and a porous crystalline inorganic oxide material having an X-ray diffraction pattern including the d-spacing maxima at 12.4±0.25, 6.90±0.15, 3.57±0.07 and 3.42±0.07 Angstrom.

Zeolite beta is disclosed in U.S. Pat. No. 3,308,069, the entire contents of which patent is incorporated herein by reference.

Mordenite is naturally-occurring but, the mordenite employed in the process of the invention is preferably one of the known synthetic forms of mordenite, such as TEA-mordenite (i. e., synthetic mordenite prepared from a reaction mixture comprising a tetraethylammonium directing agent). TEA-mordenite is disclosed in U.S. Pat. Nos. 3,766,093 and 3,894,104, the entire contents of which patents are incorporated herein by reference. More preferably, however, the TEA-mordenite used in the process of the invention has an average crystal size of less than 0.5 micron and a silica alumina molar ratio of about 25 to about 50. The required small crystal TEA-mordenite can be produced by crystallization from a synthesis mixture having a molar composition within the following ranges:

|  | Useful | Preferred |
|---|---|---|
| R/R + $Na^+$ = | >0.4 | 0.45–0.7 |
| $OH^-/SiO_2$ = | <0.22 | 0.05–0.2 |
| $Si/Al_2$ = | >30–90 | 35–50 |
| $H_2O/OH$ = | 50–70 | 50–60 |

The crystallization is conducted at a temperature of 90 to 200° C., for a time of 6 to 180 hours.

Preferably, the molecular sieve used in the process of the invention is a porous crystalline inorganic oxide material having an X-ray diffraction pattern including d-spacing maxima at 12.4±0.25, 6.9±0.15, 3.57±0.07 and 3.42±0.07 Angstrom. The X-ray diffraction data used throughout this specification were obtained by standard techniques using the K-alpha doublet of copper as the incident radiation and a diffractometer equipped with a scintillation counter and associated computer as the collection system.

Suitable porous crystalline inorganic oxide materials are MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697). All the above U.S. patents are incorporated herein by reference.

The molecular sieve used in the process of the invention does not contain the sulfided hydrogenation metal disclosed in U.S. Pat. No. 3,780,123 and is not subjected to acid-leaching as, for example, disclosed in U.S. Pat. No. 5,243,116.

As in the case of many catalysts, it may be desirable to incorporate the molecular sieve component of the catalyst of the invention with another material resistant to the temperatures and other conditions employed in the process. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material which is active tends to change the conversion and/or selectivity of the catalyst in the process. Inactive materials suitably serve as diluents to control the amount of conversion in the process so that products can be obtained in an economic and orderly manner without employing other means for controlling the rate of reaction. These materials may be incorporated into naturally occurring clays, e. g. , bentonite and kaolin, to improve the crush strength of the catalyst under commercial operating conditions. Said materials, i. e. , clays, oxides, etc. , function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the active molecular sieve component include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, such as silica, zirconia, titania, magnesia, beryllia, alumina, and mixtures thereof.

In addition to the foregoing materials, the active molecular sieve component can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of active molecular sieve component and inorganic oxide matrix vary widely, with the crystal content ranging from about 1 to about 90 percent by weight and more usually, particularly when the composite is prepared in the form of beads, in the range of about 2 to about 80 weight percent of the composite.

The feedstock used in the process of the invention comprises a mixture of ortho- and meta-DIPB and may also contain para-DIPB. Preferably, the feedstock is the non-equilibrium mixture of DIPB isomers produced as the by-product of a commercial cumene plant which typically comprises 55–65% para-DIPB, 25–35% meta-DIPB and 5–10% ortho-DIPB. Since para-DIPB is a valuable intermediate in the production of hydroquinone, the feed may be subjected to an initial distillation step to separate the para-DIPB before being fed to the process of the invention.

In the process of the invention, the DIPB-containing feedstock is contacted with benzene and, optionally cumene, in the presence of the molecular sieve catalyst described above, whereby the ortho-DIPB and any para-DIPB in the feedstock are selectively converted by transalkylation to cumene and polyisopropylbenzenes and/or by isomerization to other DIPB isomers. As a result, the effluent from the process of the invention has a higher ratio of meta-DIPB: ortho-DIPB than that of the feedstock. Typically, the ratio of meta-DIPB: ortho-DIPB in the process effluent is greater than 100, and more preferably greater than 200, so that conventional separation methods, such as superfractionation, yields a meta-rich DIPB product suitable for use in the production of resorcinol.

The molar ratio of benzene to DIPB in the process of the invention is not narrowly defined but typically is 0.5 to 100, and preferably is 1 to 10. Cumene is not necessarily present in the process of the invention but, where cumene is present, the molar ratio of benzene to cumene is typically 0.5 to 10, and preferably 1 to 5. The molar ratio of feedstock isopropyl groups:benzene rings is typically 0.05 to 1, and preferably between 0.2 and 0.8.

The conditions used in the-process of the invention should be such as to effect significant transalkylation/isomerization of ortho- and para-DIPB in the feed while minimizing the production of by-products, particularly n-propylisopropylbenzenes, trimethylindanes, triisopropyl-benzenes and other heavy materials. Suitable conditions include a temperature of about 50 to about 150° C., a pressure of about 100 to about 1000 psig, and a WHSV of about 0.1 to about 100.

More preferably, said alkylation conditions include a temperature of about 100 to about 140° C., a pressure of about 200 to about 500 psig, and a WHSV of about 0.5 to about 10.

As previously stated, the feedstock to the process of the invention is preferably the product of a commercial cumene process. More preferably, the feedstock is the product of the liquid phase alkylation of benzene with propylene in the presence of a solid alkylation catalyst, wherein the catalyst includes a molecular sieve selected from the group consisting of zeolite beta and a porous crystalline inorganic oxide material having an X-ray diffraction pattern including the d-spacing maxima at 12.40±0.25, 6.9±0.15, 3.57±0.07 and 3.42±0.07 Angstrom. Most preferably, the molecular sieve is selected from the group consisting of MCM-22, PSH-3, SSZ-25, MCM-36, MCM-49 and MCM-56. Preferred conditions for such an alkylation process include a temperature of about 100 to about 250° C., a pressure of about 50 to about 1000 psig, and a WHSV of about 0.1 to about 100. More preferably, said conversion conditions include a temperature of about 120 to about 200° C., a pressure of about 200 to about 500 psig, and a WHSV of about 0.5 to about 5.

The product from the alkylation step includes cumene, unreacted benzene and propylene and a mixture of DIPB isomers, typically in which the meta:ortho ratio is 5–15, together with some triiospropylbenzene and other impurities. In one embodiment of the invention, the alkylation product is fed to a conventional distillation train for the removal of the unreacted benzene and propylene, recovery of the cumene product and separation of DIPB fraction. The DIPB fraction is then optionally further fractionated to remove the para-isomer, whereafter the meta-and ortho-DIPB fraction is fed, together with recycled benzene, to the process of the invention. The effluent from the process of the invention is then fed to a further distillation train for removal of cumene, benzene and the meta-rich DIPB product. In an alternative embodiment, before or after removal of the unreacted propylene, the alkylation product is fed directly to the process of the invention (with or without the addition of benzene, DIPB, and TIPB recycle streams) so that conversion of the ortho- and para-DIPB is effected in the presence of benzene and cumene. A single distillation train can then be used to recover the cumene and meta-DIPB products and remove the benzene for recycle.

The invention will now be more particularly described with reference to the following Examples. In the Examples, the cumene employed was chemical grade cumene which had been purified by percolation over activated alumina.

EXAMPLE 1 (Comparative)

Alkylation of Cumene over MCM-22

2 g of an MCM-22 catalyst (1/16" extrudates with 35wt % alumina binder) were used to alkylate cumene with commercial grade propylene. The catalyst was diluted with about 2 g of sand and charged to a down-flow 3/8" external diameter, stainless steel fixed bed reactor. The catalyst was dried at 125° C. and 1 atm pressure with 100 cc/min flowing $N_2$ for 2 hours. While retaining $N_2$ flow, the reactor pressure was set to 850 psig by a grove loader and the reactor temperature was adjusted to the desired temperature for the first set of alkylation conditions (140° C.). The feed, containing cumene and propylene in the molar ratio stated in Table 1, was introduced to the reactor at the WHSV stated in Table 1. After lining out for 24 hours, liquid products were collected in a cold-trap and analyzed off-line with a Hewlett-Packard 5890 Gas Chromatograph. The catalyst was tested at several conditions, with each condition being lined out for 24 hours before collecting a liquid product. The results are shown in Table 1.

TABLE 1

| Conditions | | | | | | |
|---|---|---|---|---|---|---|
| Temperature (° C.) | 140 | 160 | 180 | 160 | 200 | 220 |
| Pressure (psig) | 900 | 900 | 900 | 900 | 900 | 900 |
| WHSV (1/Hr) | 2 | 2 | 2 | 2 | 2 | 2 |
| Cumene/Propylene (molar) | 4 | 4 | 4 | 4 | 4 | 4 |
| Reactor Effluent (Wt. %) | | | | | | |
| C5-hydrocarbons | 0.0% | 0.1% | 0.1% | 0.1% | 0.0% | 0.4% |
| Benzene | 0.4% | 0.2% | 2.5% | 1.0% | 10.8% | 11.4% |
| EB | 0.0% | 0.0% | 0.0% | 0.0% | 0.0% | 0.2% |
| Cumene | 85.5% | 73.4% | 61.5% | 71.3% | 48.1% | 42.8% |
| C9–C10 aromatics | 0.0% | 0.0% | 0.0% | 0.0% | 0.0% | 0.5% |
| 1,3-DIPB | 6.1% | 10.1% | 16.9% | 11.0% | 23.9% | 25.7% |
| 1,2-DIPB | 0.3% | 0.5% | 0.5% | 0.4% | 0.3% | 0.3% |
| 1,4-DIPB | 6.9% | 14.1% | 16.7% | 14.7% | 13.7% | 13.3% |
| C10 + aromatics | 0.1% | 0.3% | 0.3% | 1.2% | 0.0% | 0.9% |
| TIPB | 0.6% | 1.4% | 1.5% | 0.3% | 3.1% | 4.4% |
| Para Selectivity | 51.8% | 57.2% | 49.1% | 56.1% | 36.2% | 34.0% |
| Meta Selectivity | 45.6% | 40.8% | 49.6% | 42.2% | 63.0% | 65.4% |

TABLE 1-continued

| Conditions | | | | | | |
|---|---|---|---|---|---|---|
| Cumene Conversion | 6.5% | 18.5% | 30.5% | 20.6% | 43.8% | 49.1% |
| Benzene/DIPB | 0.06 | 0.01 | 0.16 | 0.08 | 0.59 | 0.60 |
| meta/ortho | 17.6 | 20.3 | 36.8 | 24.7 | 74.6 | 97.2 |

EXAMPLE 2 (Comparative)

Disproportionation of Cumene over MCM-22

The catalyst and apparatus of Example 1 were used to effect disproportionation of cumene, in the absence of propylene, under the conditions summarized in Table 2. As before, the catalyst was tested at several conditions, with each condition being lined out for 24 hours before liquid products were collected in a cold-trap and analyzed off-line with an HP 5890 GC. The results are shown in Table 2.

TABLE 2

| Conditions | | | |
|---|---|---|---|
| Temperature (° C.) | 240 | 220 | 220 |
| Pressure (psig) | 900 | 900 | 900 |
| WHSV (1/Hr) | 2 | 2 | 1 |
| Reactor Effluent (Wt. %) | | | |
| C5– | 0.1% | 0.1% | 0.0% |
| Benzene | 18.3% | 14.5% | 17.8% |
| EB | 0.2% | 0.0% | 0.0% |
| Cumene | 47.9% | 57.5% | 51.9% |
| C9–C10 aromatics | 0.7% | 0.2% | 0.2% |
| 1-3DIPB | 19.3% | 16.2% | 17.8% |
| 1-2DIPB | 0.2% | 0.2% | 0.2% |
| 1-4DIPB | 10.0% | 9.6% | 9.7% |
| C10+ aromatics | 1.0% | 0.4% | 0.5% |
| TIPB | 2.3% | 1.3% | 1.8% |
| Para Selectivity | 33.8% | 36.8% | 35.0% |
| Meta Selectivity | 65.4% | 62.3% | 64.3% |
| Cumene Conversion | 52.1% | 42.5% | 48.1% |
| Benzene/DIPB | 1.29 | 1.16 | 1.34 |
| meta/ortho | 83.1 | 67.6 | 84.9 |

EXAMPLE 3

Transalkylation of DIPB with Benzene over MCM-22

The catalyst and apparatus of Example 1 were used to effect transalkylation of feed containing diisopropylbenzenes and benzene under the conditions summarized in Table 3. As before, the catalyst was tested at several conditions, with each condition being lined out for 24 hours before liquid products were collected in a cold-trap and analyzed off-line with an HP 5890 GC. The results are shown in Table 3.

TABLE 3

| | | | | | | | | |
|---|---|---|---|---|---|---|---|---|
| Temperature, C. | Feed | 190.0 | 190.0 | 190 | 180.0 | 180.0 | 180.0 | 170 |
| Pressure (psig.) | Feed | 850.0 | 850.0 | 850.0 | 850.0 | 850.0 | 850.0 | 850.0 |
| WHSV (1/h) | Feed | 4.00 | 2.00 | 1.00 | 4.00 | 2.00 | 1.00 | 1.00 |
| Effluent (wt %) | | | | | | | | |
| DIPB | 25.3 | 19.2 | 14.0 | 10.6 | 21.0 | 23.0 | 14.4 | 21.1 |
| COMDIPB | 0.1 | 0.1 | 0.1 | 0.1 | 0.1 | 0.2 | 0.1 | 0.1 |
| Cumene | 0.1 | 9.6 | 15.6 | 20.8 | 4.8 | 10.5 | 15.9 | 5.7 |
| Benzene | 69.8 | 70.2 | 69.3 | 67.5 | 73.1 | 65.2 | 68.6 | 72.1 |
| TIPB | 0.3 | 0.2 | 0.2 | 0.2 | 0.2 | 0.3 | 0.2 | 0.2 |

TABLE 3-continued

| | | | | | | | | |
|---|---|---|---|---|---|---|---|---|
| C10+ | 1.2 | 0.6 | 0.6 | 0.6 | 0.6 | 0.7 | 0.6 | 0.6 |
| Other | 3.2 | 0.1 | 0.2 | 0.2 | 0.1 | 0.2 | 0.2 | 0.2 |
| Selectivities | | | | | | | | |
| MDIPB | 56.4% | 66.8% | 69.9% | 70.0% | 63.3% | 66.4% | 69.6% | 64.1% |
| ODIPB | 3.7% | 0.32% | 0.32% | 0.36% | 0.43% | 0.29% | 0.33% | 0.31% |
| PDIPB | 39.9% | 32.9% | 29.8% | 29.6% | 36.4% | 33.3% | 30.1% | 35.6% |
| Purity MDIPB | 93.0% | 98.5% | 98.2% | 97.9% | 98.4% | 98.6% | 98.2% | 98.5% |
| Ratio MDIPB:ODIPB | 15.4 | 210.6 | 216.9 | 196.1 | 147.4 | 228.0 | 212.9 | 207.7 |
| Conversion of DIPB | | 25.1% | 43.0% | 56.8% | 13.4% | 23.5% | 42.7% | 15.3% |

It will be seen from Table 3 that, despite the relatively low temperature employed in Example 3, MCM-22 was active for the conversion of the ortho- and para-DIPB by transalkylation and isomerization. In particular, it will be seen that the meta-DIPB:ortho-DIPB ratio obtained by the transalkylation/isomerization process of Example 3 (147 to 217) was significantly higher than that obtained by the cumene disproportionation process of Example 2 (67 to 85), and the cumene alkylation process of Example 1 (17–100).

EXAMPLE 4

Combined Disproportionation of Cumene and Transalkylation of DIPB over MCM-22

Following the procedure outlined in Example 1, chemical grade cumene was flowed over MCM-22 in the absence of propylene to disproportionate the cumene to diisopropylbenzenes (and triisopropylbenzenes) in a first reactor, Reactor A. The effluent of reactor A was then combined with benzene and the combined feed then flowed through a second reactor, Reactor B. Conditions for each reactor and the effluent of Reactor B are shown in Table 4. Reactor A contained 1 g of MCM-22 and Reactor B contained 2 grams of MCM-22.

TABLE 4

| | | | | |
|---|---|---|---|---|
| Conditions | | | | |
| Reactor A | | | | |
| Cumene (cc/h) | 0.58 | 0.58 | 0.6 | 0.3 |
| Temperature, C. | 180 | 180 | 180 | 180 |
| Reactor B | | | | |
| Benzene (cc/h) | 0.8 | 0.4 | 0.15 | 0.4 |
| Temperature, C. | 170 | 170 | 170 | 170 |
| B-Reactor Effluent | | | | |
| (wt %) | | | | |
| DIPB | 8.43% | 12.17% | 17.69% | 8.78% |
| Cumene | 19.94% | 38.22% | 44.61% | 27.20% |
| Benzene | 69.97% | 48.82% | 36.45% | 63.44% |
| EB | 0.14% | 0.01% | 0.01% | 0.01% |
| TIPB | 0.47% | 0.55% | 0.94% | 0.36% |
| C9C10 | 0.27% | 0.06% | 0.07% | 0.04% |
| C10+ | 0.75% | 0.18% | 0.22% | 0.16% |
| C5– | 0.02% | 0.00% | 0.01% | 0.00% |
| Selectivities | | | | |
| MDIPB | 68.48% | 67.83% | 66.31% | 69.19% |
| ODIPB | 0.31% | 0.38% | 0.46% | 0.33% |
| PDIPB | 31.21% | 31.79% | 33.24% | 30.48% |
| MDIPB Purity | 99.49% | 99.44% | 99.31% | 99.53% |
| MDIPB:ODIPB Ratio | 221.7 | 178.8 | 144.9 | 212.6 |
| Cumene Conversion | 51.6% | 34.5% | 43.8% | 35.3% |

It will be seen from the above Examples that the reactions containing benzene in the feedstock are unexpectedly more active for the conversion of ortho and para DIPB. It is possible that this surprising result is caused by extra benzene reducing the size and concentration of dimeric and trimeric reaction byproducts and intermediates. If so, the activity of solid acids for the equilibration of mixed isopropylbenzenes will increase continuously as the average isopropyl:ring ratio in the feedstock drops.

What we claim is:

1. A process for the selective production of meta-diisopropylbenzene, said process comprising the steps of:

(a) contacting a $C_9+$ aromatic hydrocarbon feedstock containing meta- and ortho-diisopropylbenzene with benzene under conversion conditions with a catalyst comprising a molecular sieve selected from the group consisting of zeolite beta, and a porous crystalline inorganic oxide material having an X-ray diffraction pattern including the d-spacing maxima at 12.4±0.25, 6.9±0.15, 3.57±0.07 and 3.42±0.07 Angstrom, said contacting step selectively converting ortho-diisopropylbenzene in the feedstock to produce an effluent in which the ratio of meta-diisopropylbenzene to ortho-diisopropylbenzene is greater than that of the feedstock; and then (b) feeding said effluent to a separation zone to recover from said effluent a product rich in meta-diisopropylbenzene.

2. The process of claim 1, wherein the porous crystalline inorganic oxide material is selected from the group consisting of MCM-22, PSH-3, SSZ-25, MCM-36, MCM-49 and MCM-56.

3. The process of claim 1, wherein said porous crystalline inorganic oxide material is MCM-22.

4. The process of claim 1, wherein said molecular sieve is zeolite beta.

5. The process of claim 1, wherein said feedstock is contacted in step (a) with benzene and cumene.

6. The process of claim 1, wherein said conversion conditions include a temperature of about 100 to about 250° C., a pressure of about 50 to about 1000 psig, and a WHSV of about 0.1 to about 100 l/hr.

7. The process of claim 1, wherein said conversion conditions include a temperature of about 120 to about 200° C., a pressure of about 200 to about 500 psig, and a WHSV of about 0.5 to about 5 l/hr.

\* \* \* \* \*